United States Patent
Stoy et al.

(10) Patent No.: US 6,726,721 B2
(45) Date of Patent: Apr. 27, 2004

(54) HYDROGEL-BASED PROSTHETIC DEVICE FOR REPLACEING AT LEAST A PART OF THE NUCLEUS OF A SPINAL DISC

(75) Inventors: Vladimir A. Stoy, Princeton, NJ (US); Petr Stehlicek, Kladno (CZ); Zdena Kozlova, Beroun (CZ); Tomas Drunecky, Kladno (CZ)

(73) Assignee: Replication Medical Inc., Bloomfield, MI (US)

( * ) Notice: Subject to any disclaimer, the term of this patent is extended or adjusted under 35 U.S.C. 154(b) by 0 days.

(21) Appl. No.: 09/853,002

(22) Filed: May 10, 2001

(65) Prior Publication Data

US 2003/0055506 A1 Mar. 20, 2003

Related U.S. Application Data

(63) Continuation-in-part of application No. 09/410,268, filed on Sep. 30, 1999, now Pat. No. 6,264,695.

(51) Int. Cl.[7] .................................................. A61F 2/44
(52) U.S. Cl. .................................. 623/17.16; 623/17.11
(58) Field of Search ................ 623/17.16, 17.11–17.15, 623/23.41, 23.51, 23.58

(56) References Cited

U.S. PATENT DOCUMENTS

| | | |
|---|---|---|
| 3,875,595 A | 4/1975 | Froning |
| 4,107,121 A | 8/1978 | Stoy |
| 4,349,921 A | 9/1982 | Kuntz |
| 4,772,287 A | 9/1988 | Ray et al. |
| 4,863,476 A | 9/1989 | Shepperd |
| 4,904,260 A | 2/1990 | Ray et al. |
| 4,911,718 A | 3/1990 | Lee et al. |
| 4,943,618 A | 7/1990 | Stoy et al. |
| 5,047,055 A | 9/1991 | Bao et al. |
| 5,053,034 A | 10/1991 | Olerud |
| 5,192,326 A * | 3/1993 | Bao et al. ................ 623/17.12 |
| 5,252,692 A | 10/1993 | Lovy et al. |
| 5,458,643 A * | 10/1995 | Oka et al. ................ 623/17.16 |
| 5,534,028 A * | 7/1996 | Bao et al. ................ 623/17.16 |
| 5,674,295 A | 10/1997 | Ray et al. |
| 5,674,296 A | 10/1997 | Bryan et al. |
| 5,676,701 A | 10/1997 | Yuan et al. |
| 5,824,093 A | 10/1998 | Ray et al. |
| 5,824,094 A | 10/1998 | Serhan et al. |
| 5,865,846 A | 2/1999 | Bryan et al. |
| 6,165,225 A * | 12/2000 | Antanavich et al. ...... 623/23.72 |
| 2002/0035401 A1 * | 3/2002 | Boyce et al. ............ 623/23.51 |
| 2003/0023311 A1 * | 1/2003 | Trieu ...................... 623/17.16 |

FOREIGN PATENT DOCUMENTS

| | | |
|---|---|---|
| EP | 0 505 634 A1 | 9/1992 |
| WO | WO 00/64385 | 11/2000 |
| WO | WO 02/076336 A2 | 10/2002 |

* cited by examiner

Primary Examiner—Corrine McDermott
Assistant Examiner—Alvin Stewart
(74) Attorney, Agent, or Firm—Carter, DeLuca, Farrell & Schmidt, LLP

(57) ABSTRACT

The present invention is a prosthetic for replacement of at least a part of the nucleus of a intravertebral disc. The prosthetic device is composed of at least two essentially parallel soft layers of an elastically deformable hydrogel and at least one rigid layer, the rigid layer having less compressibility than the soft layers, being adjacent to the soft layers, parallel to them, and firmly attached to them. In some embodiments, the soft layers have the same thickness and composition. Typically, the prosthesis has more than one rigid layer and these rigid layers have the same thickness and composition. The number of soft layers is usually one more than the number of rigid layers, with, e.g., at least three soft layers.

75 Claims, 1 Drawing Sheet

HYDROGEL-BASED PROSTHETIC DEVICE FOR REPLACEING AT LEAST A PART OF THE NUCLEUS OF A SPINAL DISC

REFERENCES TO RELATED APPLICATIONS

This Application is a continuation-in-part of U.S. patent application Ser. No. 09/410,268 filed on Sep. 30, 1999 now U.S. Pat. No. 6,264,695, entitled "Spinal Nucleus Implant", with Vladimir A. Stoy as inventor.

BACKGROUND OF THE INVENTION

1. Field of the Invention

The present invention is direct to a hydrogel-based prosthetic device to replace all or part of the nucleus of a spinal disc after it has been surgically removed. More specifically, the present invention is directed to such a device which contains a uniquely advantageous combination of differing structural compositions and geometries.

2. Information Disclosure Statement

The spinal disc is a cartiligeous spinal joint which allows the bending and rotation of the spine. Damage to the spinal disc leads to a dysfunction of the spine, serious pain, and often to a long-term disability of the patient. A typical problem consists of the spinal disc bulging out or herniating so that the nucleus becomes extruded, which then causes a compression of an adjacent nerve and an inflammatory reaction. Presently, it is typical to immobilize the joint by fusing the neighboring vertebrae using various instruments and techniques. It is also common to remove the nucleus or its part in a procedure called a laminectomy.

All present surgical interventions, whether laminectomy or fusion of adjacent vertebrae, lower the functionality of the spine in some way. For that reason it is desirable to try to develop a prosthetic for the spinal disc or its part. This is, however, extremely difficult. The spine is a very complex part of the body and its proper function is dependent on proper coordination of the function of all the parts, including the spinal discs. The system needs to withstand complex stresses, including various angles of bending, pressure, shear, and twisting. The spinal disc must also function as a shock and vibration absorber. And finally, a spinal disc must allow the transport of the nutrients and metabolic products needed for its health and survival. These complex requirements elucidate the complex structure of the spinal disc.

The spinal disc is made of a hydrogel-like core called Nucleus Pulposus (NP), and an outer sheath called Annulus Fibrosus (AF). The AF consists mainly of collagen fibers which are organized into many criss-crossed layers somewhat like layers in automotive tires. This configuration ensures significant resistance against radial stress and inner over-pressure, while allowing significant deformation during twisting and bending. The NP is located within the AF. The NP is a hydrogel-like composite made of proteoglycane and collagen, with a uniform water content of more than 90% of total mass. Its composition is similar to the AF except it has a lower collagen content and a higher content of proteoglycane and water. Aside from that, the NP is isotropic, while the AF is significantly anisotropic. The NP is connected to the AF, and the transition between these two bodies is gradual.

The areas of adjacent vertebrate bodies can also be thought of as parts of the intra-vertebral joint system. These areas are covered with cartilage consisting of a collagen matrix filled with glycoprotein and water. Just like the NP and the AF, these cartilages are a living tissue that contains approximately 2–5% of live cells needed to renew the cartilage. The collagen fibrilles of the AF are attached to the vertebrate area cartilage. The NP is attached to the AF, but not to the vertebrate area cartilage. This arrangement is important for the mobility and proper function of the intravertebral joint.

The function of the spinal disc can be compared to the function of a tire in a car. In this case the "tire" itself is made of the AF, while the NP functions like the compressed air in the tire. The NP has viscoelastic mechanometric characteristics. Aside from that it is, like air, capable of changing its volume with a changing load. This is achieved by the change of the water content due to outside pressure. Resistance produced by the nucleus to the reduction of water content by mechanical pressure ("wringing") is called "swelling pressure". Such pressure is produced by the partially dehydrated NP gel, which is trying to absorb water to regain equilibrium and increase its volume. Swelling pressure is also a key point in the function of the intra-vertebral spinal disc. When the axial pressure load increases, part of the liquid is expelled from the nucleus, which increases the swelling pressure (the concentration of the polymer increases). The process will stop only when equilibrium is reached and the axial pressure equals the swelling pressure. In this way, the NP is able to balance out and apportion the pressure in the spine, and it does so especially by transferring axial load into radial load, which is then captured by the AF. Furthermore, the changes in swelling are the driving force of the transportation of metabolites and nutrients, without which the NP tissues could not survive in the long term.

From the above-stated facts it is obvious, that the construction of a fully functional prosthesis is extremely difficult. Most prosthetic devices suggested to date are strictly mechanical, and they mimic only some functions of the disc. An example of such are constructions described in US patents by Froning (U.S. Pat. No. 3,875,595), Kuntz (U.S. Pat. No. 4,349,921), Shepperd (U.S. Pat. No. 4,863,476), Olerud (U.S. Pat. No. 5,053, 034), Bryan et al. (U.S. Pat. Nos. 5,674,269 and 5,865,846), Yuan et al. (U.S. Pat. No. 5,676,701) and Serhan, et al. (U.S. Pat. No. 5,834,094).

A more perfect prosthetic with a truer simulation of the disk function was suggested in a U.S. Pat. No. 4,911,718 "Functional and Biocompatible Intervertebral Spacer" (Lee et al, 1990), describing a composite construction of the prosthetic of the disc using a biocompatible elastomer, reinforced by fibers which mimic the function of collagen fibers in a natural spinal disc. The main disadvantage of this solution, which is common to all full spinal disc replacements, remains a complicated surgical procedure, which translates into a high cost, and a high risk to the patient.

In many cases, only the NP (or even a portion of the NP) can be replaced to restore function. The replacement of a missing NP will keep the AF in a necessary state of tension, which will also enable its proper mechanical function. It is also necessary to replace the function of the original NP in regards to nutrient and metabolic waste transport, since without this feature the remaining living tissues of the spinal disc cannot survive. For that reason, the NP substitute must be made of a hydrogel with a sufficient swelling pressure and a capability of hydraulic transport of fluids.

A hydrogel substitute for the NP was first suggested by Bao et al in the U.S. Pat. No. 5,047,055. Bao describes a hydrogel prosthesis of the nucleus, whose shape and size corresponds to the removed disc nucleus when the prosthesis is fully swollen. According to the requirements stated in the patent, the hydrogel used in a fully swollen state must have a water content of at least 30% by weight, and a pressure strength of at least 4 MN.m$^{-2}$. This high strength must be achieved even at full swelling in water and during a high water content (Bao suggests 70% to 90% by weight as optimum). This high strength is apparently requested in order to prevent isotropic extrusion of the material implanted into the damaged and weakened AF. The selection of hydrogels fulfilling this requirement is narrow, however.

Furthermore, Bao teaches to implant his prosthetic in a partially dehydrated state when the dimensions are smaller and the device can be inserted through a smaller opening. After implantation, the prosthetic will grow to its full size by absorbing bodily fluids. It is necessary to note, however, that the dehydration prior to implantation and rehydration after implantation are isotropic, i.e. all dimensions change at the same rate. This can be seen as a significant disadvantage of the Bao concept. During implantation the implant will try to expand equally in all directions, but it will expand most in the direction of the least resistance. Therefore it will expand the least in the axial direction, where expansion is most needed (so that the separation of the vertebrae is the highest), and it will expand the most in the radial direction, where the expansion is least desirable; especially in places where the AF is weakened or even missing. For this reason Bao was forced to suggest an implant which is in its fully swollen state exactly the size of the cavity created by the removal of the NP or its part. This presents a significant obstacle, however, and also means a lowered function of the implant, which will then will have a zero swelling pressure at a fully swollen state.

Another disadvantage, stemming from the isotropic characteristics of the materials, is its radial bulging under axial pressure. This bulging will be the greatest in the direction of the least resistance, i.e. in the direction where the AF is weakened or damaged. The implant can also have the tendency to slowly change shape and herniate when subject to permanent and long-term pressure. The high strength and modulus requirements which Bao states are apparently governed by the effort to prevent such undesirable deformation.

Some of the stated deficiencies were later remedied in the following U.S. Pat. No. 5,192,326 (Bao et al). In this case the prosthetic is formed by hydrogel spheres placed within an elastic, semi-permeable sack or wrap. The porous wrap, in its fully unfurled state, has the shape and size of the cavity created by the removal of the NP or its part. The size of hydrogel spheres is at least three times the size of the size of the pore, therefore they cannot escape out of the wrap. The hydrogel can contain up to 99% fluid by weight in its fully swollen state, and its strength doesn't need to be as high as in the previous case since the strength of the implant is given by the strength of the wrap and not of the hydrogel. The volume of the fully swollen hydrogel cannot be larger than the size of the cavity created by the removal of the NP, since the full swelling is prevented by the resistance of the wrap against further expansion.

A similar implant is described by Ray et al. in U.S. Pat. No. 4,772,287. Ray describes an implant into NP, consisting of two cylindrical bladders filled with a fluid. The bladders are enclosed in a fibrous wrap.

In a U.S. Pat. No. 4,904,260, Ray describes an improvement upon the previous invention, which relies on the bladders being semi-permeable, and the liquid in it contains a substance with a therapeutic effect. This substance is capable of slowly diffusing from the prosthetic into the surrounding tissue.

A further improvement is described by the same author in a U.S. Pat. No. 5,674,295. Here, the bladders filled with liquid are replaced by cylindrical hydrogel bodies. The solid fibrous wrap allows for higher swelling in the axial direction and prevents excessive swelling in the radial direction, thus protecting the AF from bulging due to the swelling pressure of the implant.

This invention is further modified in a U.S. Pat. No. 5,824,093 where the hydrogel bodies have an oval rather than a circular cross-section, and their wrap is constructed so that their general shape is maintained even during full swelling and loading. The implants described by Ray are not an actual replacement of the NP, because they have significantly different shape and characteristics. More specifically, this is a device for a partial fusion and partial immobilization of the spinal disc, rather than the restoration of its function.

The above overview indicates that a fully optimal NP prosthetic was not yet described.

SUMMARY OF THE PRESENT INVENTION

The present invention is a prosthetic for replacement of at least a part of the nucleus of a intravertebral disc. The prosthetic device is composed of at least two essentially parallel soft layers of an elastically deformable hydrogel and at least one rigid layer, the rigid layer having less compressibility than the soft layers, being adjacent to the soft layers, parallel to them, and firmly attached to them. In some embodiments, the soft layers have the same thickness and composition. Typically, the prosthesis has more than one rigid layer and these rigid layers have the same thickness and composition. The number of soft layers is usually one more than the number of rigid layers, with, e.g., at least three soft layers. The invention also includes a method of prosthesis production, which involves prefabricating soft and rigid layers; stacking at least two prefabricated soft and at least one prefabricated rigid layer in a parallel fashion into their final form, and, permitting the layers to firmly connect to one another by mutual interaction. In this method, at least one type of the layers is prefabricated in the dehydrated state, which is done by dehydrating stretched foil in an apparatus preventing its contraction and thereby decreasing its area. There is at least partial dehydration of the prosthesis under pressure applied in a direction tangent to the planes of the layers. In preferred embodiments, while in the state of almost fill dehydration, is sterilized using ionizing radiation or a gaseous chemical agent, after which it is partially rehydrated within the sterile wrapper using water vapor.

BRIEF DESCRIPTION OF THE DRAWINGS

The present invention is more fully understood when the invention is taken in conjunction with the appended drawings, wherein.

DETAILED DESCRIPTION OF THE PRESENT INVENTION

Figure 1:
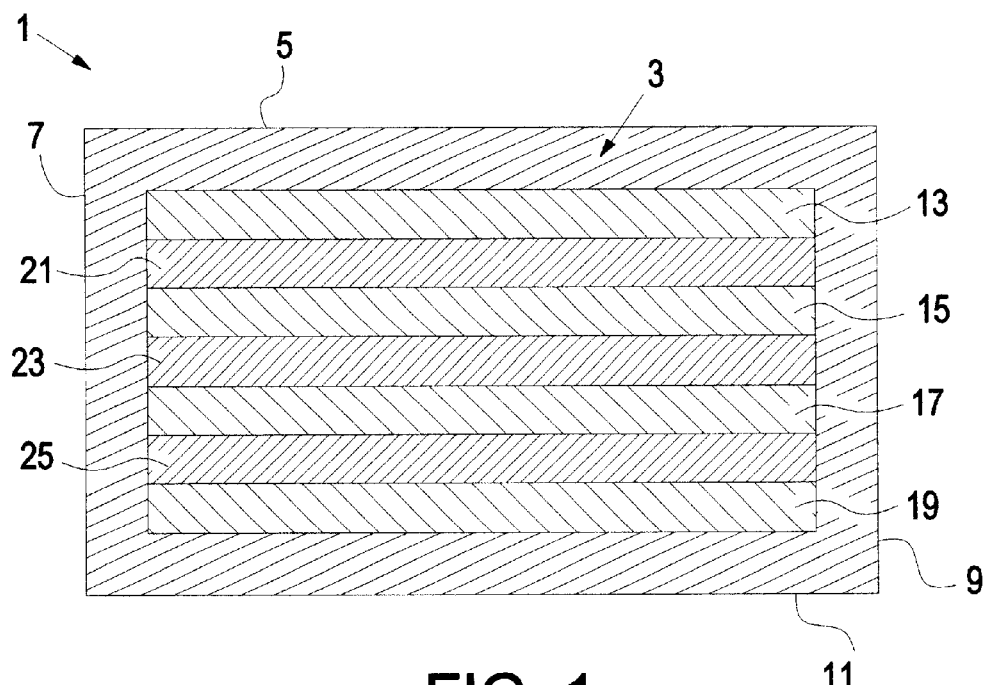
FIGS. 1 and 2 show side cut views of a present invention prosthetic device in its relaxed and compressed states, respectively. Thus, device 1 has an outer encasement 3, with a top 5, sides 7 and 9, and bottom 11, formed of a flexible skin and contains soft layers 13, 15, 17 and 19, and rigid layers 21, 23 and 25.

The stated inadequacies are removed by a prosthesis of the nucleus or its part of the intravertabral disc according to this invention as follows:

The invention is based on a hydrogel

The invention is based on being constructed of parallel soft layers of an elastically deformed hydrogel, which may be of an equal thickness, and one or more rigid layers, which may be of an equal thickness and which are adjacent to the soft layers and are essentially parallel to them.

The layers are firmly attached to one another by mutual cross-linking of both layers, and especially by using the physical interaction between polymer chains or and adhesive interface, which is capable of reacting with both neighboring strata.

We are then describing a structure with alternating layers, which can be more or less subject to tensile deformation.

These layers are essentially parallel. An advantageous arrangement will contain at least three soft layers. The combination of soft and rigid layers also allows variations where the number of rigid layers is one less than the soft layers, and vice versa. If the number of soft layers is larger by one, then the contact between the prosthetic and the cartilage of the vertebra is enabled by the softer hydrogel with a higher water content. This has a number of advantages, for example a gentler contact with the cartilages, and better hydraulic transport of water in and out of the prosthetic. By the same token, the terminus of the prosthetic must be secured by encapsulation of the layered nucleus in a soft hydrogel cover.

Similarly it is possible to use a wrap made of a more rigid material, possibly even a wrap made of a textile material. Such a wrap can favorably effect the mechanical durability of the prosthetic and its resistance to herniation in case of a weakened AF.

If the number of less-deformable layers is one more then the others, then the contact with the vertebral cartilage is formed by the more rigid, less yielding and less slippery surface. This can be an advantage especially in cases where the AF is weakened, and it is necessary to ensure increased friction between the prosthetic and the vertebrae. It is of course also possible to arrange a contact of one vertebra with a soft surface, and the other vertebra with a hard surface, depending on the state of the vertebrae and the sheath of the disk. In this case the number of soft and hard layers would be the same.

According to this invention, the prosthetic can have different layers of different thicknesses, which would aid the design of various profiles under load and various distributions of pressure in the prosthesis. In most cases it is advantageous for all soft layers to be of an equal thickness, which will result in minimal bulging for a given number of layers under load. The uniformity of each type of layers regarding the thickness and composition will also aid easy production.

An advantageous part of the construction are also cavities or channels in the hydrogel, which positively affect the ability of the prosthesis to deform under low loads and support the transportation of fluids. In most cases it is advantageous to arrange the channels of an appropriate diameter and number vertically, that coaxially with the axis of the spine. Such channels mutually and advantageously connect a certain number of parallel layers, as well the surface of the prosthetic.

The soft layer is formed by high-strength, high water content hydrogels. An example of such hydrogels is polyvinylalcohol (PVA), physically cross-linked by partial crystallization of the chain. Such hydrogels are described, for example, in U.S. Pat. No. 4,663,358. Another example are hydrogels based on segmented polyurethanes or polyureas, an example of which is described in U.S. Pat. No. 5,688,855. In principle, polypeptide or polysaccharide hydrogels could be used, an example of which is agarose or cross-linked hyaluronic acid, even though biodegradation often limits the lifetime of such implants. According to this invention, very advantageous hydrogels for the prosthetic are based on partially hydrolyzed or aminolyzed polyacrylonitrile (PAN), an example of which is described in U.S. Pat. Nos. 4,943,618; 4,107,121, and 5,252,692.

The hydrogel in the soft layer has an advantageously equilibrium water content higher than 75% by weight and at full swelling, and if possible higher than 85% by weight. Most advantageous are hydrogels with a water content over 90% by weight, being similar to a water content of the natural nucleus of the disk. Such hydrogels do not need to posses high strength at full swelling by water since in their functional state they are significantly dehydrated both osmotically and through mechanical pressure. This limited swelling in the functional state is entirely essential to the function of the prosthetic. Therefore, the size of the prosthetic at full swelling by water is significantly higher than the size of the original nucleus, or rather the size of the cavity created by the partial or entire removal of the original nucleus. For the same reason the shape of the fully hydrated (swollen) prosthetic in water is significantly different than the shape into which the prosthetic is inserted in a dehydrated and deformed state. On the other hand, these hydrogels should have a sufficient hydraulic permeability for water to allow dehydration and rehydration via pressure. Further they must possess sufficient biocompatibility, and especially they must not release any harmful substances. They must also be sufficiently stable in their implanted state to guarantee a sufficiently long function of the prosthetic (which does not necessarily mean that they need to last to the end of the life of the patient—these prosthetics are useful even if they are used for a temporary improvement of function of the spinal disc).

The rigid layer must possess the characteristics of sufficient stability, compatibility, and other qualities important for implants in general, but in also must possess a sufficient tensile elastic modulus. It can be made of various polymers, such as polyethylenterphtalate (Dacron), polyamide, polyurethane, polyureas, acrylic and methacrylic polymers, expanded polytetrafluoroethyl (Goretex), graphite, rare metal alloys, etc. These materials can be used either alone, or in a composite form in combination with elastomers or hydrogels. Especially advantageous are woven, perforated, or porous formats of these materials which will allow solid anchoring of the soft layer.

The rigid layer will work well if it will have an easy tensile deformation to a certain deformation point, at which time the resistance to further deformation will increase sharply. Such behavior can be seen, for example, in polymers crystallizing under tensile stress, such as natural rubber, or knits and other textile configurations. This type of mechanical behavior allows the construction of a prosthetics with optimal mechanical characteristics. Especially good construction of the rigid layer would include a woven textile (for example, a Dacron net) embedded in a relatively rigid hydrogel of a similar or identical type as the one used in the soft layer, but the two would have different levels of water content. This combination ensures excellent adhesion between the soft and the rigid layer via mutual cross-linking which can be facilitated through physical interactions. It also ensures proper anchoring of the textile insert within the hydrogel. This also ensures proper pressure distribution between the hydrogel and the textile insert. "Softness" and "rigidity" of both types of layers is relative. The soft layer is typical in exhibiting a relative extension under tensile stress larger than 200% and preferably even exceeding 400% in a fully swollen state. The rigid layer has a reversible relative deformation lower than 100%.

The invention also includes the adjustment of the implant so it is ready for implantation. A prosthetic in this state is made smaller through dehydration, and plastified using an appropriate, physiologically harmless softening agent such as water or glycerol. This is best be done at a concentration where the softening temperature (the transition between the vitreous and the deformed state) is higher than −5° C. (and even better, above the room temperature) and lower than 40° C., and preferably lower than bodily temperature. This temperature transition can be characterized by a softening temperature or a glass transition temperature Tg (the values for the same composition vary somewhat according to the method used. According to the invention, the preferred method is described in U.S. Pat. No. 4,731,079, Example 1). The prosthetic in the described state makes the implantation possible in the deformed state in the shape (rolled up like a burrito), which is then inserted through an opening of a minimum size (such as a small channel). Once the insertion is completed, the implant will unfurl relatively quickly and assume a flat and properly oriented shape, in which it can start swelling in a predominantly axial direction.

Another characteristic of the invention is the preparation for implantation where the swelling or expansion through hydration occurs essentially in one direction. This can be achieved by dehydrating the prosthetic during the production process by introducing a pressure deformation in the axial direction (in a direction tangent to the surface of the layers) in a way which will maintain the contour and area of the layers while decreasing the thickness of the layers in a ratio corresponding to the volume change caused by dehydration. The hydration of the prosthetic then causes radial shrinking, which compensates for swelling in the radial direction. Radial shrinking or expansion during swelling can be controlled within rather wide criteria. As a result, the expansion during hydration is focused mostly on the desirable axial direction, and is limited or eliminated in the radial direction.

The layered construction of the invention is especially advantageous for radial deformation, which can be introduced either during drying or at a temperature above the softening point and a subsequent chilling under pressure.

This arrangement means that the ability of the prosthetic to be deformed under pressure is significantly different for different directions. The configuration of alternating parallel layers has a number of advantages as compared to other support element configurations. The first and essential advantage is the limitation of radial bulging caused by axial pressure. Pressure tangent to the planes of the layers (normal or axial pressure) is partially transformed into a shear stress among the layers. Soft layers are elastically deformed, but the increase of their cross-section is limited by low deformability of the rigid layers. This also limits the overall radial bulging of the prosthetic. This ensures a resistance against the herniation of the prosthetic in a place of a weakened AF. If the prosthetic is suddenly put under a pressure load, individual soft layers will bulge radially. The water content in the layers will drop over time, however, which will cause a lessening of the radial bulging. Another advantage of this configuration is a basic lack of limitation of torsional deformation or deformation during bending. Other types of rigid support limiting radial bulging tend to also limit the torsional deformation during bending.

The prosthetic is inserted into the cavity, which was originally filled by the natural disk nucleus that was subsequently removed using surgical or biochemical methods. The prosthetic is oriented in such a way, in which the planes of all the layers are oriented more or less tangent to the axis of the spine, i.e. tangent to the vector of pressure loading (axial pressure). The layer configuration limits radial deformation of the soft layers and thus the bulging of the prosthetic and its herniation from the disk. This radial bulging will be even smaller with a decreasing height of individual soft layers at rest, i.e. with an increased overall number of layers.

Radial deformation is limited by the axial pressure being converted to shear stress between the individual layers. Maximum permissible shear stress determines the maximum axial pressure loading, which will increase with the number of layers, the strength of the layers, and the strength of bonding between individual layers.

This configuration has an advantage as compared to other composite constructions in that the dehydration of the hydrogel components via axial pressure is minimally limited. This dehydration is necessary for the function of the prosthetic, since its cyclical dehydration and rehydration supplies nutrients to the living tissue of the disc. Another advantage of the invention is the maximal flattening during dehydration, which is important for the implantation of the prosthetic through the smallest opening possible. The prosthesis is prepared for implantation in the following way: the dehydrated, flattened disc is sterilized using ionizing radiation or a gaseous chemical agent, and then is partially rehydrated within a sterile wrapper. Thus prepared disc is adjusted by being rolled up into a shape of a burrito or an omelet. Another important advantage is the fact that the hydration (swelling) expansion happens essentially in the axial direction without exhibiting radial expansion which might damage surviving tissues (annulus fibrosus) and cause the herniation of the nucleus. And finally, the construction of the prosthetic according to this invention leads to an optimal pressure distribution within the prosthetic, allowing it to handle even extreme loads common for the spinal environment.

Another embodiment of this invention is the manufacturing method of the prosthetic using layers of hydrogels. The main problem is achieving complete adhesion among the layers and the prevention of deformation of the prosthetic as a result of uneven expansion or contraction of individual layers during production. The manufacturing method of this invention is based on at least one type of the layers being previously prepared in a state of controlled dehydration, and is oriented so that the swelling expansion is demonstrated as a basic increase in thickness (rather than the increase of contour and surface area dimensions). This method of dehydration is performed in a solution which prevents the contraction of the surface and thus the decrease of the surface area.

The manufacturing of a prosthetic based on a hydrogel sandwich structure can be easily realized by using three components, such as hydrogels of the AQUACRYL. type (made by GEL-MED International) and polyester surgical netting (made by VUP a.s. Brno):

Hydrophilic polymer with a higher water content, such as AQUACRYL 90 (AQC 90)

Hydrophilic polymer with a lower water content, such as AQUACRYL 80 (AQC 80)

Polyester surgical netting (PES)

Each of these components has its own specific function in the resulting prosthetic:

- AQC 90 forms the basis of the prosthetic, acting as the main connecting element of its individual parts, it determines its basic mechanical properties, and simultaneously it ensures good biocompatibility with the surrounding tissues
- AQC 80 improves the mechanical properties of the prosthetic (especially it increases its pressure strength modulus) and simultaneously it ensures good adhesion of AQC 90 to PES
- PES forms a reinforcement whose main function is to prevent the deformation of the prosthetic in a way which would allow it to herniate out of the intravertebral space.

The combination of characteristics of individual components in the sandwich structure yields a prosthetic whose mechanical properties (especially its behavior during dynamic strain under pressure) mimics the characteristics of the actual Nucleus Pulposus as closely as possible, and which simultaneously yields good biocompatibility with surrounding tissues.

EXAMPLES OF INVENTION'S APPLICATION

Figure 2:
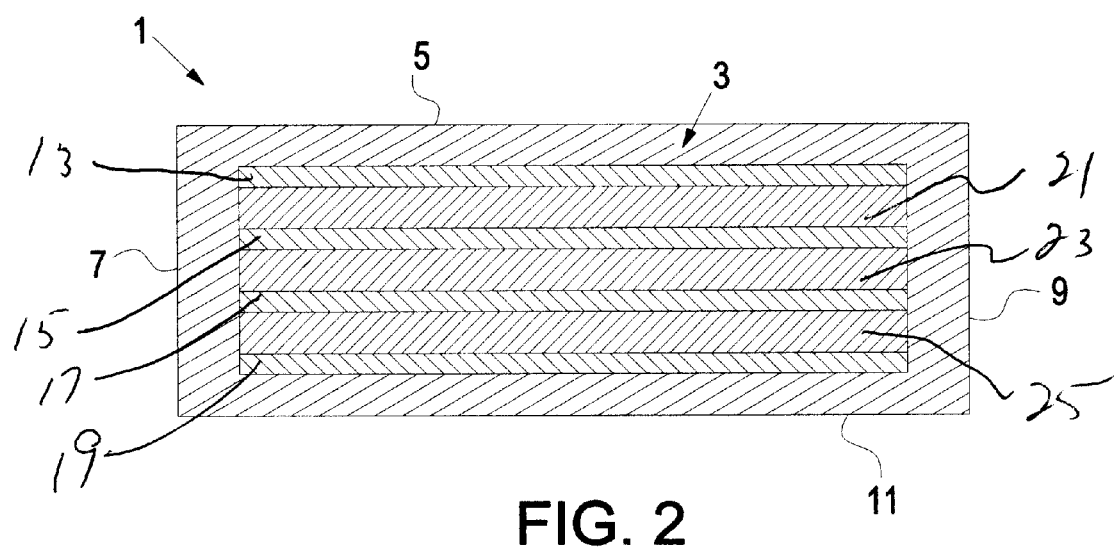

The invention is further illustrated in the following examples, which do not limit the scope of its' applicability, however. FIG. 1 shows a schematic cross-section of a fully hydrated prosthetic and FIG. 2 shows a cross-section of a dehydrated prosthetic.

Example 1

A prototype of the NP prosthetic was prepared using an AQUACRYL type hydrogel.

AQUACRYL is a copolymer, prepared by a partial alkaline hydrolysis of polyacrylonitrile (PAN) in the presence of sodium thiocyanate (NaSCN). The resulting hydrolysis product is a multi-block acrylic copolymer, containing alternating hydrophilic and hydrophobic blocks. Hydrophilic blocks contain acrylic acid, acrylamidine, and acrylamide. The hydrophobic blocks are formed by the remaining sequences of unreacted acrylonitrile units. The composition of the hydrolysis product varies with the type of AQUACRYL material, and depends on reaction conditions and the conversion of the hydrolytic reaction. The composition and basic properties of the two standard types used in this example are as follows:

| Copolymer composition (% mol) | AQUACRYL 90 | AQUACRYL 80 |
|---|---|---|
| Acrylonitrile units | 55 | 79 |
| Acrylic acid units | 30 | 14 |
| Acrylamide units | 9 | 4 |
| Acryalmidine units | 6 | 3 |

Essential Characteristics of the Coagulate

| Equilibrium in pure water | | |
|---|---|---|
| Copolymer composition (% molar) | AQUACRYL 90 | AQUACRYL 80 |
| Liquid content (% by weight) | 99 | 90 |
| Tensile strength (kg · cm$^{-2}$) | <0.1 | 7 |

| Equilibrium in an isotonic solution (0.9% NaCl in water) | | |
|---|---|---|
| Copolymer composition (% molar) | AQUACRYL 90 | AQUACRYL 80 |
| Liquid content (% by weight) | 90 | 80 |
| Tensile strength (kg · cm$^{-2}$) | 6 | 17 |

AQUACRYL is supplied in the form of a 10% (by weight) polymer solution dissolved in a sodium thiocyanate solution (55% aqueous NaSCN by weight). AQUACRYL can be poured directly from such solution onto glass or plastic substrates in order to form hydrogel foil or plate shapes, or various shapes in semi-enclosed or porous molds. The gelling of the solution occurs through the so-called coagulation, i.e. the replacement of NaSCN by water.

The prosthetic is manufactured using several steps. The first step forms prefabricated soft and rigid layers which will be assembled into the final configuration in subsequent steps. Individual steps can be described as follows:

The Preparation of Non-Reinforced Hydrogel Foils

The AQUACRYL solution was poured onto a level glass plate, and spread out into desired thickness using a strip whose height above the glass surface was adjustable using thickness control elements. The solution was carefully covered with water and in about 10 minutes it was transferred into a wash basin filled with an excess of an isotonic solution (0.9% NaCl in water by weight). The coagulated foils were washed out in fresh isotonic solution and placed in a plasticizing solution, which contains 12.5% glycerine and 87.5% isotonic NaCl solution (by weight). The foils remain in this solution for 24 hours.

The Preparation of Reinforced Hydrogel Foils

Round stretching frames 15 cm in diameter were stretched with knit polyester netting supplied by the Knitting Research Institute a.s. in Brno. The stretched net was carefully placed on top of an aquacryl solution layer of a desired thickness located on top of a glass plate. The depth of immersion of the net into the aquacryl solution was controlled by spacers placed underneath the frame. The solution within the stretch frame was carefully covered with water, and in 10 minutes was transferred into a wash basin filled with an excess of an isotonic solution (0.9% NaCL in water by weight). The coagulated foils in the frames were washed out in fresh isotonic solution. They were then placed in the plasticizing solution formed by 12.5% glycerine and 87.5% isotonic NaCl solution (by weight), where they remained for 24 hours.

Dehydration of Hydrogel Foils

The non-reinforced foils were removed from the plasticizing bath and the excess liquid was removed using a filter paper. Thus dried off foils were supported by polyester netting on both sides and stretched within the round stretch frames. The frames were secured around the perimeter using clamps to prevent the material from slipping out and placed in a dryer preheated to 65° C. for two hours. Then they were removed and cooled to a room temperature at a relative humidity of 30–60%. Prior to further processing the foils were stored while stretched on frames in closed PE bags.

The reinforced foils were dried using the same method of being stretched onto the frames in which they were made. They were secured with clamps around the perimeter to prevent the material from slipping out during contraction and drying.

Dehydrated foils plasticized with glycerin hold their shape at room temperature. When immersed in an isotonic solution, such as plasma, they swell only in thickness, while their base shape does not change. This phenomenon of frozen shape memory in the plasticized state is specific for this type of hydrogel, and is also well suited for this application.

The dehydrated plasticized foils were cut into elliptical shapes 30 mm long and 15 mm wide, with two holes 3 mm in diameter located in the ⅓ and ⅔ of the main axis.

Assembling the Nucleus of the Prosthesis

A stainless steel apparatus was constructed using two base plates and two connecting guide rails. Each base plate has an elliptical shape 34 mm long and 17 mm wide, with circular openings 3 mm in diameter centered on the main axis and located 5 mm from the center. Each plate is 5 mm thick. Two stainless steel guide rails, 2.95 mm in diameter, are 25 mm long.

The guide rails are inserted into one base plate, and the individual layers cut from the dehydrated, plasticized aquacryl foil are threaded onto them. Their type and order varies according to the intended prosthetic configuration and it's intended final mechanical properties.

As explained above, the desired characteristics are achieved by alternating soft and rigid layers.

In this example we manufactured 4 types of layers:

| Layer | Hydrogel | Polyester netting reinforcement |
|---|---|---|
| A | AQUACRYL 90 | No |
| B | AQUACRYL 90 | Yes |
| C | AQUACRYL 80 | No |
| D | AQUACRYL 80 | Yes |

Layers can be assembled in various orders, such as:

(1) B-A-B-A-B-A-B
(2) A-B-A-A-B-A-A-B-A
(3) A-D-A-D-A-D-A
(4) D-C-A-C-D-C-A-C-D-C-A-C-D
(5) D-C-D-C-A-C-D-C-A-A-C-D-C-A-C-C
(7) A-C-A-C-A-C-A-C-A
(8) C-D-C

As apparent above, foils B and D with an embedded net will always act as a rigid layer. Foil A made of the non-reinforced AQUACRYL 90 (AQC 90) will act as a soft layer. The non-reinforced foil C made of AQUACRYL 80 (AQC 80) can act as a rigid layer (such as in configuration 7) or as soft layers (config. 8), or as transitional layers between the soft and rigid type (for example, configs. 4 and 5). The thickness of the individual soft or rigid layers can change according to the number of foils used and their thickness. This shows that this manufacturing method is quite flexible, and can be used to achieve various characteristics without changing the basic approach or product.

Mutual cross-linking of individual layers can be accomplished by using appropriate adhesives, which can be either reactive or solvent-based. Of the reactive ones, cyanoacrylates or polyurethanes with free isocyanate groups could be used, especially ones which form elastic and solid sublayers. Of the solvent-based ones, the best ones are aqueous sodium thiocyanate, possibly in combination with potassium and calcium thiocyanate. Other suitable adhesives are also the solutions of AQUACRYL and other related acrylic copolymers.

The method used in this example is as follows:

Aquacryl layers are loosely threaded onto guide rails in the desired sequence (such as A-D-A-D-A-A-D-A-A-D-A-D) so there is free space between them, and they are secured with the other base plate on the other side. The whole configuration is briefly immersed in a 55% NaSCN in water (by weight), and placed inside a press, where the excess of the liquid is expressed using a force of about 10 kg. The configuration is left under this weight for about 30 minutes, after which the nucleus is removed from the guide rails.

The composite nucleus is encapsulated in AQUACRYL 90 in the next step.

Nucleus Encapsulation

Once the layers are glued together, the resulting nucleus is allowed to swell in a physiological solution until it reached equilibrium. The swollen nucleus is patted dry, and immersed into a 55% NaSCN (by weight) for a period of time. Thus prepared nucleus is then placed into a form with porous walls (pore size on the order of m), or semi-permeable walls (permeable to low molecular weight substances), and embedded in a AQC 90 solution so that a contiguous layer of AQC 90 is formed around the whole nucleus. Once the form is closed and the excess AQC 90 solution is expressed, the form is placed in a water bath where the AQC 90 coagulation will occur over a period of approximately 15 hours. Once the form is removed from the bath and the form is disassembled, the finished prosthetic is further washed in the waster to eliminate the remaining NaSCN. Then it is washed in a physiological solution until equilibrium is reached.

The resulting product is depicted on a schematic drawing in FIG. 1, where A represents AQUACRYL 90 soft hydrogel layers, D represents AQUACRYL 80 rigid hydrogel layers reinforced with a polyester net, and E represents the outer AQUACRYL 90 sheath surrounding the prosthetic.

Anisotropic Prosthesis Dehydration

Once an equilibrium water concentration is achieved, the prosthesis is dried while weighed down. The weight is applied in a direction tangent to the plane of the nucleus which is located in a tube-like form of an elliptical cross-section. The internal dimensions of the form correspond to the dimensions of the nucleus' base shape. The direction of the load, selection of appropriate load level, and the placement of the disc in the form during drying result only the height of the prosthesis changing, but the base shape and dimensions staying the same. Drying in the air occurs for several days, after which the disk is finished in a dryer at 70° C. under steady load. The result of the dehydration process is a flat elliptical disc made of a hard xerogel, depicted schematically in FIG. 2.

Sterilization of the Prosthesis

The dried disc is wrapped in a semi-permeable sack (a wrapper used for gas or steam sterilization) and sterilized using gamma radiation. Once sterilized, the wrapper is exposed to a high relative humidity until the disc absorbs approximately 20% of its weight in water, and becomes plastic and bendable. Once in this state, it is enclosed in a water-tight wrapper and stored under controlled conditions.

The implantation can be performed by inserting a rolled-up dehydrated prosthesis through an appropriate channel into the cavity created by the removal of the NP or its part. It is advisable to fill or flush the rest of the cavity with an appropriate physiologically harmless isotonic solution which will speed up the unfurling and swelling of the prosthesis in situ.

Example 2

The dehydrated and radiation sterilized elliptical disc from Example 1 is partially rehydrated using water vapor. Then it is heated up to 60° C. and rolled under sterile conditions into a roll of about 7.5 mm in diameter, and chilled to a temperature of +4° C. The rolled-up elliptical disc is then rinsed with aqueous ethanol for additional sterilization, dried off, and enclosed in sterile packaging. During implantation the rolled-up prosthesis is inserted through a channel into the intravertebral space and oriented appropriately, after which a sterile physiological solution at body temperature is injected into the space. Once heated up to body temperature, the prosthetic will unfurl from the rolled-up to a flat state. It will swell by absorbing water, and will expand in the axial direction relative to the spine. The speed of unfurling of the prosthetic and its subsequent expansion is controlled by the concentration of water in the hydrogel after its partial rehydration.

Example 3

The prosthetic can also be manufactured by using other materials than those described in examples 1 and 2. Elliptical profiles sized 30×17 mm are cut out of an open-cell polyurethane foam. One polyurethane foam type (A) is soft, yielding, with density of about 0.03 g.cm$^{-3}$. The other foam type (B) is semi-rigid with a density of about 0.15 g.cm$^{-3}$.

The profiles are saturated by an AQUACRYL 90 solution from Example 1, and then they are stacked in a B-A-B-A-B order, enclosed in an encapsulation form from Example 1, and further processed by coagulation, washing, dehydration, and sterilization as in Example 1.

The prosthetics described in this invention can be used in the medical industry.

What is claimed is:

1. A spinal disc implant for replacement of at least a part of the nucleus of a intravertebral disc, which comprises:
    an implant which is adapted to replace at least a part of the nucleus of an intravertebral disc and which is composed of at least two essentially parallel soft layers of an elastically deformable hydrogel and at least one rigid layer, said rigid layer having less compressibility than said soft layers, being adjacent to the soft layers, parallel to them, and firmly attached to them.

2. The implant according to claim 1 wherein the soft layers have the same thickness and composition.

3. The implant according to claim 1 wherein there is more than one rigid layer and these rigid layers have the same thickness and composition.

4. The implant according to claim 1 wherein the number of soft layers is one more than the number of the at least one rigid layer.

5. The implant according to claim 1 wherein there are at least three soft layers.

6. The implant according to claim 1 wherein at least one of said at least one rigid layer is reinforced by a reinforcement component selected from the group consisting of textile fibers, a perforated polymer foil or a combination of the two.

7. The implant according to claim 6 wherein textile fibers are the reinforcing component and have a configuration selected from the group consisting of a knit net, a nonwoven textile, or a woven lattice placed parallel to the firm layer surface.

8. The implant according to claim 1 wherein the elastically deformable hydrogel in a state of maximum swelling has a water content of more than 75% by weight.

9. The implant according to claim 1 wherein the elastically deformable hydrogel in a state of maximum swelling has a water content of more than 90% by weight.

10. The implant according to claim 1 wherein the hydrogel is selected from a group consisting of partially hydrolyzed polyacrylonitrile, partially aminolyzed polyacrylonitrile, crystallized polyvinylalcohol, hydrophilic polyurethane, and a hydrogel derived from agar.

11. The implant according to claim 1 wherein the at least one rigid layer contains a hydrogel of the same type as the hydrogel in the soft layers, but with a different water content.

12. The implant according to claim 1 wherein the layers are firmly attached by mutual cross-linking of the layers or by an adhesive selected from the group consisting of reactive adhesive and solvent based adhesive.

13. The implant according to claim 1 wherein the prosthetic has an initial volume, base contour and surface, and the volume of said prosthetic prior to implantation is lessened by at least partial dehydration.

14. The implant according to claim 13 wherein when said at least partially dehydrated prosthetic is in a flat state, and substantially disc-shaped, the base contour and surface are preserved, and the thickness of the layers is diminished in a ratio to the volumetric change caused by the dehydration.

15. The implant according to claim 1 wherein said prosthesis is plasticized by water, by a physiologically harmless plasticizer mixable with water, or a combination of such plasticizers.

16. The implant according to claim 15 wherein the softening point of the plasticized prosthetic is between −5° C. to 40° C.

17. A spinal disc implant which comprises an implant member dimensioned for positioning in a space between adjacent vertebrae, the implant member defining a longitudinal axis that is substantially coaxial with the adjacent vertebrae when implanted, and a length extending along the longitudinal axis, the implant member comprising at least two hydrogel layers, the layers oriented substantially coaxially to each other and in substantially coaxial relation to the adjacent vertebrae, whereby upon at least partial hydration of the implant member, the implant member has a capacity to swell to a length along the longitudinal axis which is greater than the space between the adjacent vertebrae.

18. A spinal disc implant according to claim 17 wherein the implant member comprises at least two hydrogel layers, a first of the hydrogel layers being less rigid than a second of the hydrogel layers.

19. A spinal disc implant according to claim 18 further comprising a reinforcing member which assists in limiting the increase in width of the implant member along the transverse axis.

20. A spinal disc implant according to claim 19 wherein the reinforcing member is located in the more rigid hydrogel layer.

21. A spinal disc implant according to claim 19 wherein the reinforcing member is selected from the group consisting of textile fibers, a perforated polymer foil and a combination thereof.

22. A spinal disc implant according to claim 21 wherein the textile fibers are in the form of a woven lattice, nonwoven textile or web.

23. A spinal disc implant according to claim 18 wherein the at least two hydrogel layers are substantially parallel.

24. A spinal disc implant according to claim 18 further comprising a third layer which is more rigid than the first of the hydrogel layers and made of a material selected from the group consisting of non-hydrogel forming polymer, metal and graphite.

25. A spinal disc implant according to claim 24 wherein the polymer is selected from the group consisting of polyethyleneterephthalate, polyamide, polyurethane, polyurea, acrylic, methacrylic, polytetrafluoroethylene and combinations thereof.

26. A spinal disc implant according to claim 18 wherein the at least two layers are attached to each other by mutual crosslinking of the layers.

27. A spinal disc implant according to claim 18 wherein the at least two layers are attached to each other by an adhesive.

28. A spinal disc implant according to claim 18 wherein the implant member comprises at least three hydrogel layers, the first and third of the hydrogel layers being less rigid than the second of the hydrogel layers.

29. A spinal disc implant according to claim 28 wherein the first and third of the hydrogel layers have substantially the same thickness and composition.

30. A spinal disc implant according to claim 29 wherein the at least three hydrogel layers are substantially parallel to one another.

31. A spinal disc implant according to claim 28 wherein the second of the hydrogel layers is interposed between the first and third of the hydrogel layers.

32. A spinal disc implant according to claim 28 further comprising a reinforcing member which assists in limiting the increase in length of the implant member along the horizontal axis.

33. A spinal disc implant according to claim 32 wherein the reinforcing member is located in the second hydrogel layer.

34. A spinal disc implant according to claim 28 wherein the implant member includes a fourth hydrogel layer, the second and fourth hydrogel layers being more rigid than the first and third of the hydrogel layers, the second and fourth layers having substantially the same thickness and composition.

35. A spinal disc implant according to claim 18 wherein the implant member comprises at least three hydrogel layers, the second and third layers being more rigid than the first of said layers.

36. A spinal disc implant according to claim 35 wherein the first layer is interposed between the second and third layers.

37. A spinal disc implant according to claim 17 wherein the space between the adjacent vertebrae is the disc space.

38. A spinal disc implant according to claim 17 wherein the implant member includes at least four hydrogel layers, at least three of the hydrogel layers being less rigid than a fourth of the hydrogel layers.

39. A spinal disc implant according to claim 38 wherein the implant member includes at least five hydrogel layers, at least three of the hydrogel layers being less rigid than a fourth and fifth of the hydrogel layers.

40. A spinal disc implant according to claim 39 wherein the fourth and fifth of the hydrogel layers are respectively interposed between each of the at least three of the less rigid hydrogel layers to form an alternating arrangement of more rigid and less rigid hydrogel layers.

41. A spinal disc implant according to claim 40 wherein a reinforcing member is located in at least one of the more rigid hydrogel layers.

42. A spinal disc implant according to claim 41 wherein a reinforcing member is located within each of the more rigid hydrogel layers.

43. A spinal disc implant according to claim 39 wherein the at least five hydrogel layers are substantially parallel.

44. A spinal disc implant according to claim 17 wherein the implant member has a water content of more than about 75% by weight in a fully hydrated state.

45. A spinal disc implant according to claim 17 wherein the hydrogel includes a polymer selected from the group consisting of partially hydrolyzed polyacrylonitrile, partially aminolyzed polyacrylonitrile, crystallized polyvinylalcohol, hydrophilic polyurethane, agar and combinations thereof.

46. A spinal disc implant according to claim 17 wherein the implant member is encapsulated by a layer of hydrogel.

47. A spinal disc implant which comprises an implant member dimensioned for positioning in a space between adjacent vertebrae, the implant member defining a longitudinal axis which is substantially coaxial with the adjacent vertebrae when implanted and a length extending along the longitudinal axis, the implant member including at least two layers substantially coaxial with each other and the adjacent vertebrae, a first of the layers being a hydrogel layer which is less rigid than a second of the layers, the second of the layers being substantially planar and more rigid than the first of the layers, whereby, upon at least partial hydration of the implant member, the implant member has a capacity to swell to a length along the longitudinal axis which is greater than the space between the adjacent vertebrae.

48. A spinal disc implant according to claim 47 wherein the space between the adjacent vertebrae is the disc space.

49. A spinal disc implant according to claim 47 further comprising a reinforcing member which assists in limiting the increase in length of the implant member along the horizontal axis.

50. A spinal disc implant according to claim 49 wherein the reinforcing member is located in the more rigid layer.

51. A spinal disc implant according to claim 49 wherein the reinforcing member is selected from the group consisting of textile fibers, a perforated polymer foil and a combination thereof.

52. A spinal disc implant according to claim 51 wherein the textile fibers are in the form of a woven lattice, non-woven textile or web.

53. A spinal disc implant according to claim 47 wherein the at least two layers are substantially parallel.

54. A spinal disc implant according to claim 47 wherein the second layer is made of a material selected from the group consisting of non-hydrogel forming polymer, metal and graphite.

55. A spinal disc implant according to claim 54 wherein the polymer is selected from the group consisting of polyethyleneterephthalate, polyamide, polyurethane, polyurea, acrylic, methacrylic, polytetrafluoroethylene and combinations thereof.

56. A spinal disc implant according to claim 47 wherein the two layers are attached to each other by mutual crosslinking of the layers.

57. A spinal disc implant according to claim 47 wherein the two layers are attached to each other by an adhesive.

58. A spinal disc implant according to claim 47 wherein the implant member includes at least three layers, a first and a second of the layers being a hydrogel less rigid than a third of the layers.

59. A spinal disc implant according to claim 58 wherein the first and second of the hydrogel layers have substantially the same thickness and composition.

60. A spinal disc implant according to claim 58 wherein the layers are substantially parallel to one another.

61. A spinal disc implant according to claim 58 wherein the third of the layers is interposed between the first and second of the hydrogel layers.

62. A spinal disc implant according to claim 58 further comprising a reinforcing member which assists in limiting the increase in length of the implant member along the horizontal axis.

63. A spinal disc implant according to claim 62 wherein the reinforcing member is located in the more rigid third layer.

64. A spinal disc implant according to claim 63 wherein the implant member includes at least two more rigid layers respectively interposed between the hydrogel layers.

65. A spinal disc implant according to claim 58 wherein the implant member contains at least two layers which are more rigid than the first and second of the hydrogel layers, the more rigid layers having substantially the same thickness and composition.

66. A spinal disc implant according to claim 47 wherein the implant member includes at least three hydrogel layers.

67. A spinal disc implant according to claim 47 wherein the implant member is encapsulated by a layer of hydrogel.

68. A spinal disc implant which comprises an implant member dimensioned for positioning between adjacent vertebrae, the implant member defining a longitudinal axis and a horizontal axis which is transverse to the longitudinal axis, the implant member comprising a hydrogel and an interiorly disposed reinforcing member which assists in limiting expansion of the implant along the horizontal axis.

69. A spinal disc implant according to claim 68 wherein the implant member comprises at least two hydrogel layers, a first of the layers being less rigid than a second of the layers.

70. A spinal disc implant according to claim 68 wherein the reinforcing member is selected from the group consisting of textile fibers, a perforated polymer foil and a combination thereof.

71. A spinal disc implant according to claim 70 wherein the textile fibers are in the form of a woven lattice, non-woven textile or web.

72. A spinal disc implant according to claim 68 wherein the implant member has a capacity to swell to length along the longitudinal axis which is greater than the space between adjacent vertebrae.

73. A spinal disc implant which comprises an implant member dimensioned for positioning between adjacent vertebrae, the implant member defining a longitudinal axis and a length extending along the longitudinal axis, the implant member comprising a hydrogel, whereby upon at least partial hydration of the implant member, the implant member has a capacity to swell to a length along the longitudinal axis which is greater than the space between the adjacent vertebrae, the implant member being encapsulated by a layer of hydrogel.

74. A spinal disc implant which comprises an implant member dimensioned for positioning between adjacent vertebrae, the implant member defining a longitudinal axis and a length extending along the longitudinal axis, the implant member comprising at least three layers, a first of the layers being a hydrogel layer which is less rigid than a second of the layers, the second of the layers being substantially planar and more rigid than the first of the layers and a third of the layers being a hydrogel layer which is less rigid that the second of the layers, whereby, upon at least partial hydration of the implant member, the implant member has a capacity to swell to a length along the longitudinal axis which is greater than the space between the adjacent vertebrae, the second layer being made of a material selected from the group consisting of non-hydrogel forming polymer, metal and graphite.

75. A spinal disc implant which comprises an implant member dimensioned for positioning between adjacent vertebrae, the implant member defining a longitudinal axis and a length extending along the longitudinal axis, the implant member including at least two layers, a first of the layers being a hydrogel layer which is less rigid than a second of the layers, the second of the layers being substantially planar and more rigid than the first of the layers, whereby, upon at least partial hydration of the implant member, the implant member has a capacity to swell to a length along the longitudinal axis which is greater than the space between the adjacent vertebrae, the implant member being encapsulated by a layer of hydrogel.

* * * * *